US010653595B2

(12) United States Patent
Pillai et al.

(10) Patent No.: US 10,653,595 B2
(45) Date of Patent: May 19, 2020

(54) TOOTH WHITENING ORAL CARE COMPOSITION

(71) Applicant: Colgate-Palmolive Company, New York, NY (US)

(72) Inventors: Shyamala Pillai, Hillsborough, NJ (US); Mahmoud Hassan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/753,574

(22) PCT Filed: Aug. 20, 2015

(86) PCT No.: PCT/US2015/046003
§ 371 (c)(1),
(2) Date: Feb. 20, 2018

(87) PCT Pub. No.: WO2017/030583
PCT Pub. Date: Feb. 23, 2017

(65) Prior Publication Data
US 2018/0250205 A1    Sep. 6, 2018

(51) Int. Cl.
| *A61K 8/22*  | (2006.01) |
| *A61Q 11/00* | (2006.01) |
| *A61K 8/73*  | (2006.01) |
| *A61K 8/81*  | (2006.01) |
| *A61K 8/89*  | (2006.01) |

(52) U.S. Cl.
CPC .............. *A61K 8/22* (2013.01); *A61K 8/731* (2013.01); *A61K 8/817* (2013.01); *A61K 8/8147* (2013.01); *A61K 8/89* (2013.01); *A61Q 11/00* (2013.01); *A61K 2800/88* (2013.01); *A61K 2800/92* (2013.01)

(58) Field of Classification Search
USPC .......................................................... 424/53
See application file for complete search history.

(56) References Cited

U.S. PATENT DOCUMENTS

| 2002/0009420 A1* | 1/2002 | McLaughlin ............ A61K 8/20 |
| | | 424/53 |
| 2005/0038181 A1 | 2/2005 | Chopra et al. |
| 2006/0045854 A1 | 3/2006 | Zaidel et al. |
| 2006/0099156 A1* | 5/2006 | MacDonald ......... A61C 19/066 |
| | | 424/53 |
| 2007/0122360 A1* | 5/2007 | Oniki ..................... A61K 8/042 |
| | | 424/53 |

FOREIGN PATENT DOCUMENTS

| JP | 2001-271009 | * 10/2001 | ............... C09D 4/02 |
| WO | WO2013070184 | * 5/2013 | ............... A61K 8/73 |
| WO | 2015/071386 | 5/2015 | |

OTHER PUBLICATIONS

International Search Report and Written Opinion of the International Searching Authority in International Application No. PCT/US2015/046003, dated Mar. 29, 2016.

* cited by examiner

*Primary Examiner* — Walter E Webb

(57) ABSTRACT

The present invention provides an oral care system comprising (a) a first composition comprising: (i) a peroxide-containing whitening agent; and (ii) at least one silicone polymer, and (b) a second composition comprising a polymer selected from polysaccharides, acrylate polymers, acrylamide polymers, and a mixture of any two or more thereof; wherein the first composition and the second composition are maintained separately from one another. The present invention also provides a method of whitening teeth using the oral care system.

10 Claims, No Drawings

TOOTH WHITENING ORAL CARE COMPOSITION

BACKGROUND

There are a variety of compositions described in the art for preventing or treating the discoloration of teeth. In particular, to combat staining and brighten or restore the natural enamel color, a variety of products containing bleaching materials are commercially available for professional and consumer use. The most commonly accepted actives used in teeth whitening today are peroxides. However, there is a need to improve the efficacy of peroxide-containing compositions e.g. to provide increased whitening of the teeth within a particular time period of contact between the composition and the tooth surface.

BRIEF SUMMARY

In a first aspect, the present invention provides an oral care system comprising:
(a) a first composition comprising:
  (i) a peroxide-containing whitening agent; and
  (ii) at least one silicone polymer, and
(b) a second composition comprising a polymer selected from polysaccharides, acrylate polymers, acrylamide polymers, and a mixture of any two or more thereof;
wherein the first composition and the second composition are maintained separately from one another until use.

Optionally, the peroxide-containing whitening agent is a peroxide complex comprising hydrogen peroxide and an N-vinyl heterocyclic polymer. Further optionally, the N-vinyl heterocyclic polymer comprises a polymer selected from the group consisting of poly-N-vinyl lactams, poly-N-vinyl imides, and mixtures thereof. Still further optionally, the N-vinyl heterocyclic polymer comprises poly-N-vinyl-2-pyrrolidone.

Optionally, the peroxide complex comprises the hydrogen peroxide and the N-vinyl heterocyclic polymer in a molar ratio of from 1:2 to 1:6, optionally in a molar ratio of about 1:4.

Optionally, the first composition comprises from 0.1 to 5 weight %, from 0.25 to 3 weight %, from 0.4 to 1 weight %, or about 0.6 weight % of the peroxide-containing whitening agent, based on the weight of the first composition.

Optionally, the first composition comprises from 0.02 to 1 weight %, from 0.05 to 0.6 weight %, from 0.07 to 0.18 weight %, or about 0.1 weight % hydrogen peroxide, based on the weight of the first composition.

Optionally, the at least one silicone polymer comprises a silicone adhesive, a silicone elastomer, silicone fluid, silicone resin, silicone gum or mixtures thereof. Further optionally, the at least one silicone polymer comprises a polyorganosiloxane.

Optionally, the at least one silicone polymer comprises a silicone pressure sensitive adhesive. Further optionally, the silicone pressure sensitive adhesive is a copolymer prepared by condensing a silicone resin with a polydiorganosiloxane Optionally, the silicone resin is a silanol-containing silicone resin.

Optionally, the polydiorganosiloxane is polydimethyl siloxane.

Optionally, the first composition comprises from 30 to 60 weight %, from 35 to 55 weight %, from 40 to 50 weight %, or about 45 weight % of the at least one silicone polymer, based on the weight of the first composition.

Optionally, the first composition is a gel or a paint-on composition.

Optionally, the second composition further comprises a solvent. Further optionally, the solvent is a $C_1$-$C_4$ alcohol. Still further optionally, the solvent is ethanol.

Optionally, the polymer is present in the second composition in a concentration of from 1 weight % to 10 weight %, or about 5 weight %, based on the weight of the second composition.

Optionally, in the second composition, the polymer comprises a polysaccharide.

Optionally, the polysaccharide is an alkyl cellulose ether. Further optionally, the polysaccharide is ethyl cellulose.

Optionally, in the second composition, the polymer comprises an acrylate polymer.

Optionally, the acrylate polymer comprises 2-propenoic acid; isobutyl methacrylate; ammonium methacrylate; a block copolymer of an acrylate and a methacrylate; or a mixture of any two or more thereof.

Optionally, the acrylate polymer is an acrylate copolymer. Further optionally, the acrylate copolymer is an acrylate/octylacrylamide copolymer. Still further optionally, the octylacrylamide is N-(1,1,3,3-tetramethylbutyl)-2-propenamide. Yet further optionally, the acrylate/octylacrylamide copolymer is an isobutyl methacrylate copolymer with 2-propenoic acid and N-(1,1,3,3-tetramethylbutyl)-2-propenamide.

Optionally, in the second composition, the polymer is a polysaccharide.

Optionally, in the second composition, the polymer is an acrylate polymer.

Optionally, the second composition is a liquid, a varnish, a paint-on composition, a mouthwash, or a mouthrinse.

In a second aspect, the present invention provides a method of whitening teeth, the method comprising
(a) applying a first composition to the teeth thereby forming a first layer on the teeth, wherein the first composition comprises:
  (i) a peroxide-containing whitening agent; and
  (ii) at least one silicone polymer,
and
(b) subsequently applying a second composition to the first layer on the teeth, the second composition comprising a polymer selected from polysaccharides, acrylate polymers, acrylamide polymers, and a mixture of any two or more thereof.

In a third aspect, the present invention provides a method of enhancing the whitening efficacy of a first composition comprising a peroxide-containing whitening agent and at least one silicone polymer, which first composition has been applied to the teeth thereby forming a first layer on the teeth, the method comprising: applying a second composition to the first layer on the teeth, the second composition comprising a polymer selected from polysaccharides, acrylate polymers, acrylamide polymers, and a mixture of any two or more thereof.

In a fourth aspect, the present invention provides the use of a second composition comprising a polymer selected from polysaccharides, acrylate polymers, acrylamide polymers, and a mixture of any two or more thereof for enhancing the whitening efficacy of a first composition comprising a peroxide-containing whitening agent and at least one silicone polymer.

Optionally, in each of the second, third and fourth aspects the peroxide-containing whitening agent is a peroxide complex comprising hydrogen peroxide and an N-vinyl heterocyclic polymer. Further optionally, the N-vinyl heterocyclic polymer comprises a polymer selected from the group consisting of poly-N-vinyl lactams, poly-N-vinyl imides, and mixtures thereof. Still further optionally, the N-vinyl heterocyclic polymer comprises poly-N-vinyl-2-pyrrolidone.

Optionally, in each of the second, third and fourth aspects the peroxide complex comprises the hydrogen peroxide and the N-vinyl heterocyclic polymer in a molar ratio of from 1:2 to 1:6, optionally in a molar ratio of about 1:4.

Optionally, in each of the second, third and fourth aspects the first composition comprises from 0.1 to 5 weight %, from 0.25 to 3 weight %, from 0.4 to 1 weight %, or about 0.6 weight % of the peroxide-containing whitening agent, based on the weight of the first composition.

Optionally, in each of the second, third and fourth aspects the first composition comprises from 0.02 to 1 weight %, from 0.05 to 0.6 weight %, from 0.07 to 0.18 weight %, or about 0.1 weight % hydrogen peroxide, based on the weight of the first composition.

Optionally, in each of the second, third and fourth aspects the at least one silicone polymer comprises a silicone adhesive, a silicone elastomer, silicone fluid, silicone resin, silicone gum or mixtures thereof. Further optionally, the at least one silicone polymer comprises a polyorganosiloxane.

Optionally, in each of the second, third and fourth aspects the at least one silicone polymer comprises a silicone pressure sensitive adhesive. Further optionally, the silicone pressure sensitive adhesive is a copolymer prepared by condensing a silicone resin with a polydiorganosiloxane Optionally, in each of the second, third and fourth aspects the silicone resin is a silanol-containing silicone resin.

Optionally, in each of the second, third and fourth aspects the polydiorganosiloxane is polydimethyl siloxane.

Optionally, in each of the second, third and fourth aspects the first composition comprises from 30 to 60 weight %, from 35 to 55 weight %, from 40 to 50 weight %, or about 45 weight % of the at least one silicone polymer, based on the weight of the first composition.

Optionally, in each of the second, third and fourth aspects the first composition is a gel or a paint-on composition.

Optionally, in each of the second, third and fourth aspects the second composition further comprises a solvent. Further optionally, the solvent is a $C_1$-$C_4$ alcohol. Still further optionally, the solvent is ethanol.

Optionally, in each of the second, third and fourth aspects polymer is present in the second composition in a concentration of from 1 weight % to 10 weight %, or about 5 weight %, based on the weight of the second composition.

Optionally, in the second composition in each of the second, third and fourth aspects, the polymer comprises a polysaccharide.

Optionally, in each of the second, third and fourth aspects the polysaccharide is an alkyl cellulose ether. Further optionally, the polysaccharide is ethyl cellulose.

Optionally, in the second composition in each of the second, third and fourth aspects, the polymer comprises an acrylate polymer.

Optionally, in each of the second, third and fourth aspects the acrylate polymer comprises 2-propenoic acid; isobutyl methacrylate; ammonium methacrylate; a block copolymer of an acrylate and a methacrylate; or a mixture of any two or more thereof.

Optionally, in each of the second, third and fourth aspects acrylate polymer is an acrylate copolymer. Further optionally, the acrylate copolymer is an acrylate/octylacrylamide copolymer. Still further optionally, the octylacrylamide is N-(1,1,3,3-tetramethylbutyl)-2-propenamide. Yet further optionally, the acrylate/octylacrylamide copolymer is an isobutyl methacrylate copolymer with 2-propenoic acid and N-(1,1,3,3-tetramethylbutyl)-2-propenamide.

Optionally, in the second composition in each of the second, third and fourth aspects, the polymer is a polysaccharide.

Optionally, in the second composition in each of the second, third and fourth aspects, the polymer is an acrylate polymer.

Optionally, in each of the second, third and fourth aspects the second composition is a liquid, a varnish, a paint-on composition, a mouthwash, or a mouthrinse.

Optionally, in each of the second, third and fourth aspects the first and second compositions are maintained separately from one another prior to application to the teeth.

Optionally, in each of the second and third embodiments, after application of the second composition, the first and second compositions are maintained on the teeth for from 8 to 14 hours, from 7 to 12 hours, or for about 8 hours. Further optionally, after maintaining the first and second compositions on the teeth, the method further comprises the step of removing the first and second compositions from the teeth. Still further optionally, the process of (a) applying the first composition to the teeth, (b) applying the second composition to the teeth, (c) maintaining the first and second compositions on the teeth, and (d) removing the first and second compositions from the teeth, is carried out from 1 to 14 times, from 4 to 10 times, from 7 to 10 times, or about 8 times.

The method of the invention may be carried out over 1-8 days, optionally over 1-5 days, or optionally over 8 days.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. Unless otherwise specified, all ratios expressed herein should be understood to be ratios by weight.

As discussed above, there is a need to improve the efficacy of peroxide-containing compositions e.g. to provide increased whitening of the teeth within a particular time period of contact between the composition and the tooth surface.

The present inventors have surprisingly found that, when certain polymer solutions are applied to a tooth surface which has been coated with a composition comprising a peroxide-containing whitening agent and at least one silicone polymer, the whitening efficacy of the composition is increased.

In a first aspect, therefore, the present invention provides an oral care system comprising:
(a) a first composition comprising:
 (i) a peroxide-containing whitening agent; and
 (ii) at least one silicone polymer, and
(b) a second composition comprising a polymer selected from polysaccharides, acrylate polymers, acrylamide polymers, and a mixture of any two or more thereof;
wherein the first composition and the second composition are maintained separately from one another.

In a second aspect, the present invention provides a method of whitening teeth, the method comprising
(b) applying a first composition to the teeth thereby forming a first layer on the teeth, wherein the first composition comprises:
 (iii) a peroxide-containing whitening agent; and
 (iv) at least one silicone polymer,
and
(b) subsequently applying a second composition to the first layer on the teeth, the second composition comprising a polymer selected from polysaccharides, acrylate polymers, acrylamide polymers, and a mixture of any two or more thereof.

In a third aspect, the present invention provides a method of enhancing the whitening efficacy of a first composition comprising a peroxide-containing whitening agent and at least one silicone polymer, which first composition has been applied to the teeth thereby forming a first layer on the teeth, the method comprising: applying a second composition to the first layer on the teeth, the second composition comprising a polymer selected from polysaccharides, acrylate polymers, acrylamide polymers, and a mixture of any two or more thereof.

In a fourth aspect, the present invention provides the use of a second composition comprising a polymer selected from polysaccharides, acrylate polymers, acrylamide polymers, and a mixture of any two or more thereof for enhancing the whitening efficacy of a first composition comprising a peroxide-containing whitening agent and at least one silicone polymer.

First Composition

In each of the above aspects of the present invention, the first composition comprises a peroxide-containing whitening agent and at least one silicone polymer.

In each of the above aspects, the peroxide-containing whitening agent may be a peroxide complex comprising hydrogen peroxide and an N-vinyl heterocyclic polymer. Preferably, the polymer is crosslinked and adsorbs, absorbs, complexes, or otherwise retains the peroxide component.

Such N-vinyl heterocyclic polymers are derived from an N-heterocyclic vinyl monomer, preferably comprising N-vinyl heterocyclic monomers having from 3 to 7 atoms in a heterocyclic ring, including a carbonyl carbon atom and a nitrogen heteroatom containing a vinyl group. Preferably the ring contains 5 or 6 atoms, comprises heteroatoms such as sulfur or oxygen, and may be substituted or unsubstituted.

In certain embodiments of any of the above aspects of the present invention, the N-vinyl heterocyclic polymer may be a polymer of specific N-vinyl heterocyclic monomers, such as: N-vinyl imides to form poly-N-vinyl polyimides; N-vinyl lactams to form poly-N-vinyl polylactams; and mixtures thereof. Suitable N-vinyl imides include: N-vinyl malonimide; N-vinyl succinimide; N-vinyl glutarimide; N-vinyl maleimide; N-vinyl β-methylglutarimide; N-vinyl α-amylsuccinimide; and N-vinyl adipimide.

Suitable N-vinyl lactams include: N-vinyl peperidone; N-vinyl caprolactam; N-vinyl-3-methyl pyrrolidinone or piperidone, or caprolactam; N-vinyl-4-methyl pyrrolidinone, or piperidone or caprolactam; N-vinyl-5-methyl pyrrolidinone or piperidone; N-vinyl-3-ethyl pyrrolidinone; N-vinyl-4,5-dimethyl pyrrolidinone; N-vinyl-5,5-dimethyl pyrrolidinone; N-vinyl-3,3,5-trimethyl pyrrolidinone; N-vinyl-methyl-5-ethyl pyrrolidinone; N-vinyl-3,4,5-trimethyl-3-ethyl pyrrolidinone; N-vinyl-6-methyl-2-piperidone; N-vinyl-6-ethyl-2-piperidone; N-vinyl-3,5-dimethyl-2-piperidone; N-vinyl-4,4-dimethyl-2-piperidone; N-vinyl-7-methyl caprolactam; N-vinyl-7-ethyl caprolactam; N-vinyl-3,5-dimethyl caprolactam; N-vinyl-4,6-dimethyl caprolactam; N-vinyl-3,5,7-trimethyl caprolactam.

Suitable poly-N-vinyl polylactams include, but are not limited to: poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, and mixtures thereof. Preferably, the polymer is selected from the group consisting of poly-N-vinyl-2-pyrrolidone, poly-N-vinyl-2-piperidone, poly-N-vinyl-2-caprolactam and mixtures thereof.

In some embodiments of any of the above aspects, the polymer is poly-N-vinyl-2-pyrrolidone. The poly-N-vinyl-2-pyrrolidone is also commonly known as polyvinylpyrrolidone or "PVP". PVP refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group. The polymers include soluble and insoluble homopolymeric PVPs. Copolymers containing PVP include vinylpyrrolidone/vinyl acetate (also known as Copolyvidone, Copolyvidonum or VP-VAc) and vinylpyrrolidone/dimethylamino-ethylmethacrylate.

Soluble PVP polymers among those useful herein are known in the art, including Povidone, Polyvidone, Polyvidonum, poly (N-vinyl-2-pyrrolidinone), poly (N-vinylbutyrolactam), poly(1-vinyl-2-pyrrolidone) and poly [1-(2-oxo-1pyrrolidinyl)ethylene]. These PVP polymers are not substantially cross-linked.

The N-vinyl heterocyclic polymer may comprise a polymer selected from the group consisting of poly-N-vinyl polylactams, poly-N-vinyl polyimides, and mixtures thereof. Preferably the N-vinyl heterocyclic polymer is selected from the group consisting of poly-N-vinyl-2-pyrrolidone, poly-N-vinyl-2-piperidone, poly-N-vinyl-2-caprolactam, and mixtures thereof.

In various embodiments of any of the above aspects, N-vinyl heterocyclic polymers which are insoluble cross-linked homopolymers may be preferred. Such polymers include those commonly referred to in the art as polyvinylpyrrolidone, cross-povidone, and cPVP, and are referred to herein as "cPVP." The homopolymer is prepared by free radical polymerization of the monomer vinylpyrollidone.

In some embodiments, the poly-N-vinyl-2-pyrrolidone has a lactam of the pyrrolidone ring that provides hydrophilic characteristics. Without limiting the composition, mechanism, or function the invention, it is believed that such groups allow the peroxide compound to bind to the cPVP. The hydrophobic characteristics attributed to the methylene groups in the ring and the linear aliphatic backbone prevent the peroxide complex from reacting with saliva while still maintaining the peroxide available to whiten the teeth. The surface characteristic of the cPVP serve as a barrier to the passage of the peroxide component and prevents the premature distribution of the peroxide component upon application of the oral care composition to the oral cavity. The cPVP linked peroxide is released over a period of time through diffusion, temperature variance, moisture levels and other factors.

In some embodiments of any of the above aspects, the first composition comprises a commercially available complex of peroxide adsorbed to cross-linked polyvinylpyrrollidone. Such products include, for example, Peroxydone XL-10 and Peroxydone K-30, marketed by Ashland Inc, USA.

In some embodiments, the peroxide complex comprises the hydrogen peroxide and the N-vinyl heterocyclic polymer in a molar ratio of from 1:2 to 1:6, from 1:3 to 1:5, or in a molar ratio of about 1:4.

In some embodiments of any of the above aspects, the first composition comprises from 0.1 to 5 weight %, from 0.25 to 3 weight %, from 0.4 to 1 weight %, or about 0.6 weight % of the peroxide-containing whitening agent, based on the weight of the first composition.

In certain embodiments of any of the above aspects, the first composition comprises from 0.02 to 1 weight %, from 0.03 to 0.8 weight %, from 0.04 to 0.7 weight %, from 0.05 to 0.6 weight %, from 0.07 to 0.18 weight %, or about 0.1 weight % hydrogen peroxide, based on the weight of the first composition.

In any embodiments of any of the above aspects, the at least one silicone polymer may comprise a silicone adhesive, a silicone elastomer, silicone fluid, silicone resin, silicone gum or mixtures thereof. The at least one silicone polymer may comprise a polyorganosiloxane. The polyorganosiloxane may be present in an amount of from 10 to 20 weight %, or about 15 weight %, based on the weight of the first composition.

In any of the above aspects, the at least silicone polymer may comprise a silicone pressure sensitive adhesive. The silicone adhesive may be present in the first composition in an amount of from 20 to 40 weight %, preferably or about 30 weight %, based on the weight of the first composition. The silicone pressure sensitive adhesive may be a copolymer prepared by condensing a silicone resin with a polydiorganosiloxane. The silicone resin may be a silanol-containing silicone resin. The polydiorganosiloxane may be polydimethyl siloxane. The silicone pressure sensitive adhesive may be a copolymer prepared by condensing a silanol-containing silicone resin with a polydimethylsiloxane, such as 8-7016 silicone adhesive fluid produced by Dow Corning.

The at least one silicone polymer may comprise polydimethylsiloxane, such as Q7-9120 silicone fluid produced by Dow Coming.

In a typical embodiment of any of the above aspects, the at least one silicone polymer comprises a combination of a polyorganosiloxane and a silicone pressure sensitive adhesive. In such embodiments, the one or more silicone polymer may comprise: (i) a copolymer prepared by condensing a silanol-containing silicone resin with a polydimethylsiloxane; and (ii) polydimethylsiloxane.

In certain embodiments of any of the above aspects, the first composition comprises from 30 to 60 weight %, from 35 to 55 weight %, from 40 to 50 weight %, or about 45 weight % of the at least one silicone polymer, based on the weight of the first composition.

The first composition may also further comprise a thickening agent, which may be selected from the group consisting of poly(vinylpyrrolidone), salts of poly(methyl vinyl ether-co-maleic anhydride), poly(vinylpyrrolidone-co-vinyl acetate), silicon dioxide, fumed silica, and stearic acid esters. Preferably, the thickening agent is poly(vinylpyrrolidone). The thickening agent may be present in the first composition in an amount of from 15 to 25 weight %, from 15 to 20 weight %, or about 18 weight %, based on the weight of the first composition.

The first composition may also further comprise a material selected from the group consisting of a surfactant, a peroxide activator, a buffer, a chelating agent, a solvent, a flavorant, a sweetener, a colorant, a desensitizing agent, a vitamin, an enzyme, an antimicrobial agent, an anti-caries agent, an anti-calculus agent and mixtures thereof.

Flavorants that may be used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. Preferred are synthetic mint oils and aromas, in particular that of the Symrise AG sold under the name OPTAMINT® oils and flavors. The flavoring agent may be incorporated in the first composition at a concentration of about 0.0 to about 2 weight %, based on the weight of the first composition.

Suitable sweeteners include sodium saccharin, sodium cyclamate, xylitol, perillartin, D-tryptophan, aspartame, dihydrochalcones, optionally in concentrations of about 0.01 to about 1% by weight, based on the weight of the first composition. Sodium saccharin is preferred.

Other ingredients which may be included in the first composition comprise materials commonly used in oral care formulations. These include: antimicrobial agents, e.g., Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol); anti-inflammatory agents such as ibuprofen, flurbiprofen, aspirin, indomethacine; anticaries agents such as sodium-, calcium-, magnesium- and stannous fluoride, aminefluorides, disodium monofluorophosphate and sodium trimetaphosphate; plaque buffers such as urea, calcium lactate, calcium glycerophosphate and strontium polyacrylates; vitamins such as Vitamin C; plant extracts; desensitizing agents, e.g., potassium citrate, potassium chloride, potassium tartrate, potassium bicarbonate, potassium oxalate, potassium nitrate and strontium salts; agents effective against dental calculus such as pyrophosphate salts including the mono, di, tri and tetra alkali metal and ammonium pyrophosphate and tripolyphosphate salts; biomolecules, e.g., bacteriocins, antibodies, enzymes such as papain, glucoamylase; opacifying agents, pigments, coloring agents and fluoride ion providing salts having anticaries efficacy such as sodium fluoride, potassium fluoride, a tin fluoride such as stannous fluoride.

The first composition may be non-aqueous, the term "non-aqueous" meaning that the composition is substantially free from water. The term "anhydrous" may also be used in place of the term "non-aqueous". Preferably such non-aqueous compositions contain 0 weight % water. Such compositions may comprise from 0 weight % to 0.5 weight % water.

In some embodiments of any of the above aspects, the first composition is a gel or a paint-on composition.

Second Composition

In each of the above aspects, the second composition comprises a polymer selected from polysaccharides, acrylate polymers, acrylamide polymers, and a mixture of any two or more thereof.

In any of the above embodiments of any of the above aspects of the present invention, the polymer may present in the second composition in a concentration of from 1 weight % to 10 weight %, from 2 weight % to 9 weight %, from 3 weight % to 8 weight % from 4 weight % to 6 weight %, or about 5 weight %, based on the weight of the second composition.

In some embodiments of any of the above aspects, in the second composition the polymer comprises a polysaccharide. In certain such embodiments, the polymer is a polysaccharide. The polysaccharide may be an alkyl cellulose ether (i.e. an alkyl ether of cellulose) such as, for example, ethyl cellulose. The alkyl group of the alkyl cellulose may be hydroxyl-substituted e.g. hydroxypropyl cellulose. In certain embodiments the polysaccharide is ethyl cellulose, for example ethyl cellulose having a degree of ethoxylation of 45-50 mol. %. Suitable ethyl celluloses for use in the second composition of the present invention include Ethocel© from The Dow Chemical Company and Aqualon N22 from Hercules/Ashland. Aqualon N22 is an ethyl cellulose with an ethoxyl content of 48.0 to 49.5 mol. % and a degree of substitution of ethoxyl groups per anhydroglucose unit of from 2.46 to 2.58.

In some embodiments of any of the above aspects, in the second composition the polymer comprises an acrylate polymer. In certain such embodiments, the acrylate polymer is an acrylate copolymer. The acrylate polymer may comprise 2-propenoic acid; isobutyl methacrylate; ammonium methacrylate; a block copolymer of an acrylate and a methacrylate; or a mixture of any two or more thereof.

In some embodiments, the acrylate copolymer is an acrylate/octylacrylamide copolymer. The octylacrylamide may be N-(1,1,3,3-tetramethylbutyl)-2-propenamide. In certain embodiments, the acrylate/octylacrylamide copolymer is an isobutyl methacrylate copolymer with 2-propenoic acid and N-(1,1,3,3-tetramethylbutyl)-2-propenamide (also known as 2-propenoic acid, 2-methyl-, 2-methylpropyl ester, polymer with 2-propenoic acid and N-(1,1,3,3-tetramethylbutyl)-2-propenamide), such as Dermacryl 79® from AkzoNobel.

In some embodiments, the second composition further comprises a solvent. The solvent may be a $C_1$-$C_4$ alcohol, such as methanol, ethanol, butanol or isopropanol. Preferably, the solvent is ethanol.

In some embodiments, the second composition is a liquid, a varnish, a paint-on composition, a mouthwash, or a mouthrinse.

In some embodiments of the second, third and fourth aspects of the present invention, the first and second compositions are maintained separately from one another prior to application to the teeth.

Methods

In the second aspect, the present invention provides a method of whitening teeth, the method comprising (a) applying a first composition to the teeth thereby forming a first layer on the teeth, wherein the first composition comprises:
  (i) a peroxide-containing whitening agent; and
  (ii) at least one silicone polymer,
and
(b) subsequently applying a second composition to the first layer on the teeth, the second composition comprising a polymer selected from polysaccharides, acrylate polymers, acrylamide polymers, and a mixture of any two or more thereof.

In the third aspect, the present invention provides a method of enhancing the whitening efficacy of a first composition comprising a peroxide-containing whitening agent and at least one silicone polymer, which first composition has been applied to the teeth thereby forming a first layer on the teeth, the method comprising: applying a second composition to the first layer on the teeth, the second composition comprising a polymer selected from polysaccharides, acrylate polymers, acrylamide polymers, and a mixture of any two or more thereof.

In certain embodiments, after application of the second composition, the first and second compositions are maintained on the teeth for from 5 to 15 hours, from 6 to 14 hours, from 7 to 12 hours, from 7 to 10 hours, or for about 8 hours. After maintaining the first and second compositions on the teeth, the method may further comprise the step of removing the first and second compositions from the teeth (e.g. by brushing with a toothbrush, optionally also with a dentifrice such as a toothpaste).

The process of (a) applying the first composition to the teeth, (b) applying the second composition to the teeth, (c) maintaining the first and second compositions on the teeth, and (d) removing the first and second compositions from the teeth, may be carried out from 1 to 14 times, from 2 to 13 times, from 4 to 12 times, from 4 to 10 times, from 7 to 10 times, from 7 to 9 times, or about 8 times.

EXAMPLES

Example 1

In order to study the effect of the second composition of the present invention on the whitening efficacy of the first composition, various polymer solutions (corresponding to the "second composition") were prepared as follows:
  (i) 5 weight % solution of isobutyl methacrylate copolymer with 2-propenoic acid and N-(1,1,3,3-tetramethylbutyl)-2-propenamide (Dermacryl 79®) in ethanol.
  (ii) 5 weight % solution of ethyl cellulose (Aqualon N22 from Hercules/Ashland.) in ethanol Test blocks of bisected human molars prepared and numbered from 1 to 6, and an initial L*a*b* reading was taken of each block via a spectroshade image. L*a*b* refers to stain score in accordance with the Commission International de l'Eclairage Laboratory (CIELAB) color scale. L* is lightness-darkness scale, a* is red-green chroma and b* is yellow-blue chroma. From measurement of the L*a*b* values, a whitening index can be calculated:

$$\Delta W^* = W^*\text{final} - W^*\text{initial}, \text{ where } W^* = (a^{*2} + b^{*2} + (L^* - 100)^2)^{1/2}$$

From measurement of the L*a*b* values, a lightening index can also be calculated:

$$\Delta L^* = L^*\text{final} - L^*\text{initial}$$

L*a*b* values can be measured using an optic shade-taking system to analyse and identify the color of a substrate.

Each block was numbered and assigned to one of the treatment regimens shown in Table 1, below:

TABLE 1

| Regimen | Description | Blocks |
|---|---|---|
| 1 | First composition (0.1 weight % $H_2O_2$) only | 1 and 2 |
| 2 | First composition (0.1 weight % $H_2O_2$) coated with Dermacryl 97 ® polymer coating | 3 and 4 |
| 3 | First composition (0.1 weight % $H_2O_2$) coated with Aqualon N22 polymer coating | 5 and 6 |

The first composition as used in these examples had the formula as shown in Table 2, below:

TABLE 2

| Ingredient | Weight % |
|---|---|
| DOW CORNING 8-7016 FLUID | 30.00 |
| Q7-9120 SILICONE FLUID - 350 CST. | 15.55 |
| COP PLASTIGEL 5 (LYNNE) | 35.00 |
| SODIUM SACCHARIN Powder-USP | 0.30 |
| Nat&Art Optamint Whitening 381818 Flavor | 0.60 |
| Polyvinyl pyrrolidone | 18.00 |
| Peroxydone XL-10F | 0.55 |
| Total | 100.00 |

Exactly 60 µl of the first composition (containing 0.55 weight % PVP—$H_2O_2$, corresponding to a concentration of 0.1 weight % $H_2O_2$ in the composition) was pipetted and applied to the surface of each of blocks 1 to 6. 0.5 mL of the 5 weight % Dermacryl 79® solution was applied over the gel on blocks 3 and 4 with a pipette, and 0.5 mL of the 5 weight % ethyl cellulose (Aqualon N22) solution was applied over the gel on blocks 5 and 6 with a pipette. The coatings were allowed to dry for about 3 minutes, then the blocks were placed in individual compartments of a 24 well plate, submerged in saliva, and allowed to incubate at 37° C. overnight (approximately 15 hours). The blocks were then removed individually and cleaned thoroughly with distilled water and brushed with a 1:2 (by weight) slurry of toothpaste in water, then rinsed. After this treatment, another spectroshade image was taken of each block and the L*a*b* analysis carried out to calculate $\Delta W^*$ and $\Delta L^*$.

The process was repeated seven more times (i.e. for a total of eight treatments) with a spectroshade image taken. $\Delta W^*$ and $\Delta L^*$ were calculated for each block after each treatment. The results obtained are detailed in Tables 3 and 4, below. The results shown are the mean of the values obtained for blocks assigned to the same treatment regimen (see Table 1, above). A more negative value for $\Delta W^*$ indicates increased whitening, and a more positive value for $\Delta L^*$ indicates increased lightening.

TABLE 3

| | $\Delta W^*$ | | |
|---|---|---|---|
| Treatment no. | Blocks 1 & 2 | Blocks 3 & 4 | Blocks 5 & 6 |
| 1 | −4.08 | −4.74 | −1.52 |
| 2 | −5.24 | −6.93 | −3.36 |
| 3 | −5.64 | −5.81 | −2.83 |
| 4 | −5.62 | −7.76 | −3.95 |

TABLE 3-continued

| | $\Delta W^*$ | | |
|---|---|---|---|
| Treatment no. | Blocks 1 & 2 | Blocks 3 & 4 | Blocks 5 & 6 |
| 5 | −5.61 | −7.23 | −5.53 |
| 6 | −5.84 | −7.91 | −5.07 |
| 7 | −6.63 | −8.31 | −6.78 |
| 8 | −6.61 | −9.02 | −7.80 |

TABLE 4

| | $\Delta L^*$ | | |
|---|---|---|---|
| Treatment no. | Blocks 1 & 2 | Blocks 3 & 4 | Blocks 5 & 6 |
| 1 | 0.75 | 1.35 | 0.95 |
| 2 | 1.45 | 3.15 | 1.95 |
| 3 | 2.00 | 3.10 | 2.00 |
| 4 | 1.85 | 3.85 | 2.25 |
| 5 | 1.90 | 4.25 | 2.95 |
| 6 | 2.05 | 4.35 | 3.00 |
| 7 | 2.30 | 4.55 | 3.50 |
| 8 | 2.20 | 5.00 | 4.60 |

As can be seen from Table 3, Regimen 2 (blocks 3 and 4) provided increased whitening efficacy as compared to Regimen 1 (blocks 1 and 2) after each treatment cycle. This shows that applying a coating of an acrylate/octylacrylamide polymer (Dermacryl 97®) over the first composition on the tooth surface results in increased whitening efficacy of the first composition.

As can also be seen from Table 3, Regimen 3 (blocks 5 and 6) provided increased whitening efficacy as compared to Regimen 1 (blocks 1 and 2) after the seventh and eighth treatment cycles. This shows that applying a coating of a cellulose polymer (Aqualon N22) over the first composition on the tooth surface results in increased whitening efficacy of the first composition upon repeated treatment cycles.

As can be seen from Table 4, both Regimen 2 (blocks 3 and 4) and Regimen 3 (blocks 5 and 6) provided increased efficacy in lightening the teeth as compared to Regimen 1 (blocks 1and 2) after each treatment cycle. This shows that applying a coating of an acrylate/octylacrylamide polymer (Dermacryl 97®) or a cellulose polymer (Aqualon N22) over the first composition on the tooth surface results in increased tooth lightening efficacy of the first composition.

What is claimed is:

1. An oral care system comprising
   (a) a first non-aqueous composition comprising:
      (i) a peroxide-containing whitening agent; and
      (ii) at least one silicone polymer,
   and
   (b) a second composition consisting essentially of:
      (i) 2-propenoic acid, 2-methyl-2-methylpropyl ester, polymer with 2-propenoic acid and N-(1,1,3,3-tetramethylbutyl)-2-propenamide); and
      (ii) a solvent, wherein the solvent is ethanol;
   wherein the first composition and the second composition are maintained separately from one another.

2. The oral care system of claim 1, wherein the peroxide-containing whitening agent is a peroxide complex comprising hydrogen peroxide and an N-vinyl heterocyclic polymer, optionally wherein the N-vinyl heterocyclic polymer comprises a polymer selected from the group consisting of poly-N-vinyl lactams, poly-N-vinyl imides, and mixtures thereof.

3. The oral care system of claim 2, wherein the peroxide complex comprises the hydrogen peroxide and the N-vinyl heterocyclic polymer in a molar ratio of from 1:2 to 1:6, optionally in a molar ratio of about 1:4.

4. The oral care system of claim 1, wherein the first composition comprises from 0.1 to 5 weight %, from 0.25 to 3 weight %, from 0.4 to 1 weight %, or about 0.6 weight % of the peroxide-containing whitening agent, based on the weight of the first composition.

5. The oral care system of claim 1, wherein the at least one silicone polymer comprises a silicone adhesive, a silicone elastomer, silicone fluid, silicone resin, silicone gum or mixtures thereof, optionally wherein the at least one silicone polymer comprises a polyorganosiloxane.

6. The oral care system of claim 5, wherein the silicone resin is a silanol-containing silicone resin.

7. The oral care system of claim 5, wherein the silicone adhesive is a copolymer prepared by condensing a silicone resin with a polydiorganosiloxane, wherein the polydiorganosiloxane is polydimethyl siloxane.

8. The oral care system of claim 1, wherein the first composition comprises from 30 to 60 weight %, from 35 to 55 weight %, from 40 to 50 weight %, or about 45 weight % of the at least one silicone polymer, based on the weight of the first composition.

9. The oral care system of claim 1, wherein the first composition is a gel; and wherein the second composition is a liquid, a varnish, a mouthwash, or a mouthrinse.

10. The oral care system of claim 1, wherein 2-propenoic acid, 2-methyl-, 2-methylpropyl ester, polymer with 2-propenoic acid and N-(1,1,3,3-tetramethylbutyl)-2-propenamide) is present in the second composition in a concentration of from 1 weight % to 10 weight %, or about 5 weight %, based on the weight of the second composition.

* * * * *